United States Patent [19]

Sioutas

[11] Patent Number: 5,115,803
[45] Date of Patent: May 26, 1992

[54] AEROSOL ACTUATOR PROVIDING INCREASED RESPIRABLE FRACTION

[75] Inventor: Constantinos Sioutas, St. Paul, Minn.

[73] Assignee: Minnesota Mining and Manufacturing Company, St. Paul, Minn.

[21] Appl. No.: 575,971

[22] Filed: Aug. 31, 1990

[51] Int. Cl.$^5$ ............................................ A61M 15/00
[52] U.S. Cl. ......................... 128/200.23; 128/203.15
[58] Field of Search ............ 128/200.14, 200.18, 128/200.23, 203.12, 203.15, 203.23; 239/338; 261/115

[56] References Cited

U.S. PATENT DOCUMENTS

| | | | |
|---|---|---|---|
| 1,263,079 | 4/1918 | Leon | 128/200.18 |
| 2,546,214 | 3/1951 | Curry | 128/200.18 |
| 2,582,529 | 1/1952 | Curry et al. | 128/200.18 |
| 2,585,429 | 2/1952 | Boe | 299/150 |
| 2,865,370 | 12/1958 | Gattone | 128/173 |
| 3,107,670 | 3/1962 | Silson et al. | 128/200.23 |
| 3,236,458 | 2/1966 | Ramis | 239/338 |
| 3,610,480 | 10/1971 | Lippert | 128/200.23 |
| 3,838,686 | 10/1974 | Szekely | 128/200.18 |
| 4,940,051 | 7/1990 | Lankinen | 128/200.18 |
| 4,953,545 | 9/1990 | McCarty | 128/200.23 |

FOREIGN PATENT DOCUMENTS

| | | | |
|---|---|---|---|
| 586002 | 10/1959 | Canada | 128/200.23 |
| WO88/03419 | 5/1988 | Finland . | |
| 502074 | 5/1920 | France | 128/200.21 |
| 645004 | 9/1962 | Italy | 128/200.18 |
| 88/02267 | of 1988 | World Int. Prop. O. | 128/200.23 |

Primary Examiner—Edgar S. Burr
Assistant Examiner—Eric P. Raciti
Attorney, Agent, or Firm—Gary L. Griswold; Walter N. Kirn; Douglas E. Reedich

[57] ABSTRACT

An actuator for use in inhalation therapy comprising a nozzle block having an orifice and at least one bleed hole, a conduit chamber, a deagglomeration chamber, and an exit chamber, together configured as a means for increasing the respirable fraction of an aerosol formulation. This invention also provides an actuator as described above in combination with an aerosol canister comprising a pharmaceutical formulation, and a method of administering a pharmaceutical formulation via inhalation therapy. The actuator finds particular use in improving the respirable fraction of drug in aerosol formulations. The actuator also retains non-respirable particles, thus reducing the amount of drug that is inadvertently administered orally.

17 Claims, 1 Drawing Sheet

5,115,803

AEROSOL ACTUATOR PROVIDING INCREASED RESPIRABLE FRACTION

BACKGROUND OF THE INVENTION

1. Technical Field

This invention relates to inhalation devices for use with metered-dose aerosol canisters in inhalation therapy. In another aspect, this invention relates to inhalation devices that increase the fraction of drug that can be delivered in respirable form from an aerosol canister. In yet another aspect, this invention relates to inhalation devices that retain non-respirable particles. This invention further relates to methods of administering pharmaceutical formulations via inhalation therapy.

2. Description of the Related Art

It is often desirable to increase the fraction of drug in an aerosol formulation that can be delivered from an aerosol canister in respirable form. Various deagglomeration units are known to the art and are said to be useful for such a purpose. Also, geometry has been modified in order to improve the performance of aerosol actuators for use in inhalation therapy. For example, U.S. Pat. No. 2,865,370 (Gattone) describes a dispersing adaptor for use with disposable aerosol units wherein the container discharges against a curved surface Similarly, U.S. Pat. No. 4,940,051 (Lankinen) describes an inhalation device involving a curved baffle plate which deflects the aerosol discharge into an inhalation chamber. Generally spherical chambers and curved surfaces have found use in other aerosol applications. For example, U.S. Pat. No. 2,585,429 (Boe) describes an atomizing nozzle for use with liquified gases. The nozzle involves tertiary expansion of the gas from a storage container and is said to produce satisfactory fine sprays even when the liquified gas is maintained in the storage container at pressures as low as 20 psig. Primary expansion occurs in a chamber which can be generally spherical and wherein eddy currents tend to break up liquid droplets Secondary expansion occurs in a chamber that can be formed at an angle of 30° to 60° to the longitudinal axis of the primary expansion chamber. Tertiary expansion is into the atmosphere.

SUMMARY OF THE INVENTION

This invention provides an aerosol actuator adapted to receive an aerosol canister having a hollow valve stem, comprising:

a nozzle block having walls defining at least one bleed hole and walls defining a valve stem receptacle having a socket for receiving the hollow valve stem of the aerosol canister, the socket having walls defining an orifice having a longitudinal axis through the nozzle block;

walls defining a conduit chamber in open communication with the orifice and the bleed hole, wherein the conduit chamber is substantially coaxial with the orifice and dimensioned such that it does not substantially reduce the velocity of an aerosol stream introduced via the orifice;

walls defining a deagglomeration chamber in the form of an arcuate surface in open communication with the conduit chamber and having a bottom point; and walls defining an exit chamber in open communication with the deagglomeration chamber and having a longitudinal axis, wherein:

the walls defining the exit chamber intersect the arcuate surface such that there exists, in the plane of the axes of the exit chamber and the orifice, a portion of the arcuate surface between the bottom point of the arcuate surface and the walls of the exit chamber;

the deagglomeration chamber has a greatest cross-sectional area, in the plane normal to the axis of the orifice, greater than the cross-sectional area of the conduit chamber in the plane normal to the axis of the orifice; and the cross-sectional area of the exit chamber in the plane normal to its axis is less than the greatest cross-sectional area of the deagglomeration chamber in the plane normal to the axis of the orifice.

This invention also provides an actuator as described above in combination with an aerosol canister comprising a pharmaceutical formulation, and a method of administering a pharmaceutical formulation via inhalation therapy comprising the step of discharging a metered-dose aerosol canister comprising the formulation through an actuator as described above.

The actuator of this invention finds particular use in improving the respirable fraction of drug in an aerosol formulation, particularly in aerosol formulations that involve propellants, drugs, adjuvants, or excipients that do not yield optimal suspensions for aerosol delivery. The actuator also retains non-respirable particles, thus reducing the amount of drug that is inadvertently administered orally.

DETAILED DESCRIPTION OF THE PREFERRED EMBODIMENT

Figure 1:
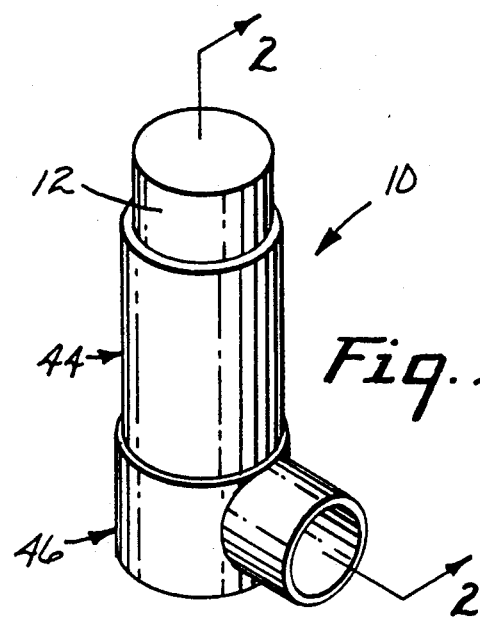
FIG. 1 is an isometric view of the actuator of the invention in combination with an aerosol canister.

Referring to FIGS. 1-5 there is shown an embodiment of the actuator of the invention, generally designated by the reference numeral 10. FIG. 1 shows actuator 10 of the invention which comprises a housing which is adapted to receive aerosol canister 12.

Aerosol canister 12 can be any aerosol canister that contains a pharmaceutical formulation for use in inhalation therapy. Such canisters comprise a valve for dispensing the aerosol, the valve having a hollow valve stem that is movable relative to the canister between an extended closed position and a depressed open position for discharge of the aerosol. The formulation in such a canister is generally under a pressure of greater than about 40 psig, and with some propellants perhaps greater than about 80 psig. Accordingly, preferred embodiments of the invention are particularly suited for use with a formulation under a pressure in the range of about 40 psig to about 80 psig.

As described in detail below and illustrated in FIGS. 2-5, the housing further defines or comprises a nozzle block and walls defining a conduit chamber, a deagglomeration chamber, and an exit chamber through which a patient can inhale a formulation discharged into the actuator form the aerosol canister.

Figure 5:
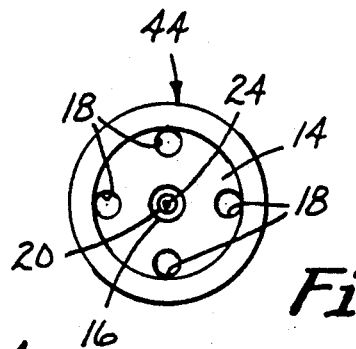
FIG. 5 is a top view of the top section of the embodiment of FIG. 4.

Actuator 10 of the invention comprises a nozzle block. As illustrated in FIG. 5, nozzle block 14 comprises walls defining valve stem receptacle 16 and walls defining bleed holes 18 to allow the passage of air through nozzle block 14 when the actuator is used in inhalation therapy. The number and dimension of the bleed holes is not unduly critical to the function of the actuator, so long as at least one bleed hole is present and capable of allowing the passage of air when the actuator is used in inhalation therapy.

Figure 2:
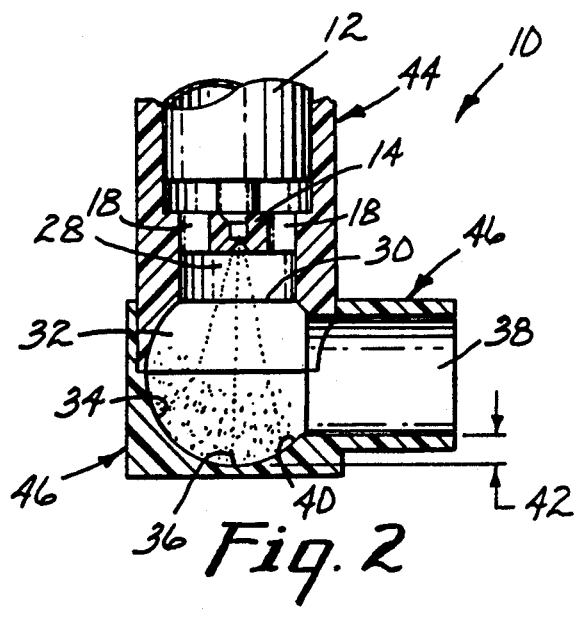
FIG. 2 is a cross-sectional view of the embodiment shown in FIG. 1, taken along line 2—2, wherein the aerosol canister is actuated.
Figure 3:
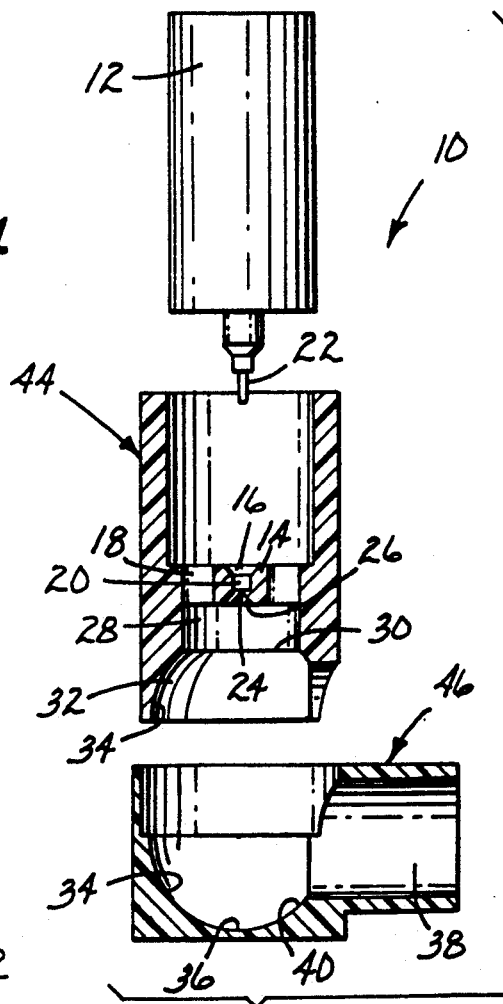
FIG. 3 is an exploded cross-sectional view of the embodiment shown in FIG. 1.

As illustrated in FIGS. 2 and 3, valve stem receptacle 16 further comprises socket 20 for receiving hollow valve stem 22 of metered-dose aerosol canister 12. Socket 20 has walls defining orifice 24 through which the discharge from the aerosol canister passes. Orifice 24 is preferably smaller in diameter than the bore of the hollow valve stem in order to increase the velocity of the aerosol stream as it passes through the orifice. Preferred diameters are in the range of about 0.20 mm to about 0.36 mm, and most preferably about 0.25 mm to about 0.30 mm.

A cross-sectional view of the embodiment of FIG. 1 is shown in FIG. 2. This embodiment is shown exploded in cross-section in FIG. 3. Orifice 24 having optional flared section 26 is in open communication with conduit chamber 28. Flared section 26 is preferred in order to further facilitate the passage of a high velocity aerosol stream through the chamber. Conduit chamber 28 is dimensioned such that it does not function as an expansion chamber, i.e., it does not substantially reduce the velocity or disrupt the flow of a passing aerosol stream. Conduit chamber 28 is substantially coaxial with the axis of orifice 24 and is preferably in the form of a right circular cylinder with a diameter of about 19 mm to about 24 mm, preferably about 21 mm. In order to achieve optimum respirable fraction, conduit chamber 28 preferably has a length of between about 6 mm and about 25 mm from orifice 24 to the region 30 where deagglomeration chamber 32 begins.

Deagglomeration chamber 32 is in open communication with conduit chamber 28 and is defined by walls having an arcuate surface 34. The arcuate surface can be any generally curved surface, e.g., a spherical, elliptical, or parabolic section and preferably is substantially spherical. The deagglomeration chamber preferably has a greatest cross-sectional area, in the plane normal to the axis of orifice 24, greater than the cross-sectional area of the conduit chamber in the plane normal to the axis of the orifice, and is preferably about 530 mm$^2$ to about 1130 mm$^2$, more preferably about 800 mm$^2$. A substantially spherical deagglomeration chamber preferably has a radius of curvature greater than the radius of the conduit chamber. Preferred radii, corresponding to the preferred cross-sectional areas set forth above, are in the range of about 13 mm to about 19 mm, more preferably about 16 mm. Further, the deagglomeration chamber is preferably substantially symmetrically disposed about the axis of orifice 24. A bulb-like combination of the deagglomeration chamber with the conduit chamber is formed in such a preferred embodiment. As described below, however, the symmetry of the deagglomeration chamber will be broken by the interface between the deagglomeration chamber and exit chamber 38.

The arcuate surface has a bottom point 36, i.e., a point such that a line normal to the axis of orifice 24 and passing through the point is more distant from the orifice than like lines corresponding to points of the arcuate surface other than the bottom point. It is preferred that bottom point 36 lie on the axis of orifice 24.

Deagglomeration chamber 32 is in open communication with exit chamber 38. The walls defining the exit chamber preferably intersect arcuate surface 34 such that there exists, in the plane of the axes of orifice 24, and exit chamber 38, a portion 40 of the arcuate surface between bottom point 36 and the walls of the exit chamber. Stated another way, the exit chamber is a take-off from the deagglomeration chamber but it does not take off from the bottom of the deagglomeration chamber; rather there is a rise between bottom point 36 of the arcuate surface and the lowermost wall of the exit chamber. This rise, designated as dimension 42 in FIG. 2, is preferably about 3 mm to about 5 mm.

In order to facilitate the use of the actuator, the axis of exit chamber 38 is preferably disposed at an angle of about 90° to about 105° to the axis of orifice 24 (i.e., the exit chamber is at a right angle or a slightly obtuse angle to the portion of the actuator that accepts the aerosol canister). Exit chamber 38 preferably is in the form of a circular or elliptical cylinder, and the cross-sectional area of the exit chamber in the plane normal to its axis is less than the greatest cross-sectional area of the deagglomeration chamber in the plane normal to the axis of orifice 24. The cross-sectional area of a cylindrical exit chamber 38 is preferably about 120 mm$^2$ to about 500 mm$^2$, more preferably about 370 mm$^2$. The exit chamber preferably is about 230 mm to about 500 mm, more preferably about 350 mm, in length.

Figure 4:
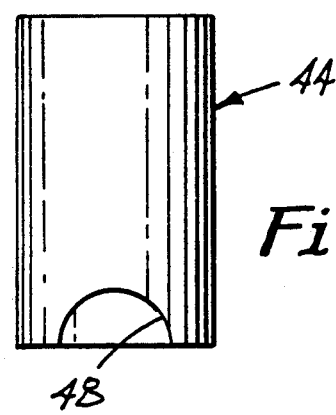
FIG. 4 is a front view of the top section of the embodiment of FIG. 1.

It is preferred that an actuator of the invention be made as an easily separable two-piece construction as illustrated in the Drawing. Top section 44 and bottom section 46 can be pressed together in a friction fit. As illustrated in FIG. 4, top section 44 has walls defining an arcuate portion 48 substantially corresponding to the top portion of the opening between the deagglomeration chamber and the exit chamber. Top section 44 can be rotated relative to bottom section 46 in order to properly align arcuate portion 48 with the exit chamber during use.

An actuator of the invention can be made of conventional materials that are generally considered suitable for use with drugs. Suitable materials include moldable thermoplastic polymers such as polyethylene, polypropylene, and the like. It is preferred in the region near the bottom point of the arcuate surface to have a surface such as glass that causes few or no drug particles to stick to the surface when the particles in the aerosol stream hit said region. However, safety, cost, and ease of manufacture cause polymeric materials, particularly polyethylene, to be preferred materials of construction for the actuator in its entirety. Conventional molding techniques are suitable for making an actuator of the invention.

The manner of use of an actuator of the invention is best understood by reference to FIG. 2. A conventional metered-dose aerosol canister containing an aerosol pharmaceutical formulation is placed in top section 44 such that valve stem 22 engages socket 20 in receptacle 16 in alignment with orifice 24. Valve stem 22 is supported by socket 20. Bottom portion 46 is rotated in order that arcuate portion 48 does not obstruct exit chamber 38. When the canister is depressed the valve is actuated and an aerosol stream containing particles or droplets of a drug is discharged through orifice 24.

Passing through the constricted opening of orifice 24 serves to accelerate the aerosol stream and also to break up some of the agglomerated particles or coalesced droplets. The stream then passes through conduit chamber 28 and into deagglomeration chamber 32.

In preferred embodiments, respirable particles in the aerosol remain suspended in the deagglomeration chamber for a time sufficient to allow a patient to inhale the formulation after discharge of the canister (e.g., for several seconds). That the particles remain suspended in the deagglomeration chamber for a time is a notable advantage of the invention, as it obviates the need for the patient to carefully coordinate actuation of the canister with inhalation of the discharged dose. When the patient inhales through the exit chamber drawing air through the actuator via bleed holes 18, the particles are carried out of the deagglomeration chamber, through exit chamber 38, and into the respiratory tract.

Not all agglomerated particles are rendered respirable by passing through orifice 24 and into deagglomeration chamber 32. It is a further advantage of this invention that many of the particles that remain outside the respirable range are trapped in the deagglomeration chamber, thus reducing the amount of the drug that is inadvertently administered orally (i.e., via large, non-respirable particles remaining in the mouth or throat). The trapped particles can easily be cleaned out of the actuator by removing and cleaning bottom section 44.

The actuator of the invention finds particular use in connection with the aerosol formulations disclosed in commonly assigned, copending application filed of even date (incorporated herein by reference).

The claimed invention is:

1. An aerosol actuator adapted to receive an aerosol canister having a hollow valve stem, comprising:
    a nozzle block having walls defining at least one bleed hole and walls defining a valve stem receptacle having a socket for receiving the hollow valve stem of the aerosol canister, the socket having walls defining an orifice having a longitudinal axis through the nozzle block;
    walls defining a conduit chamber in open communication with the orifice and the bleed hole, wherein the conduit chamber is substantially coaxial with the orifice and dimensioned such that it does not substantially reduce the velocity of an aerosol stream introduced via the orifice;
    walls defining a deagglomeration chamber in the form of an arcuate surface in open communication with the conduit chamber and having a bottom point; and
    walls defining an exit chamber in open communication with the deagglomeration chamber and having a longitudinal axis,
    wherein:
    the walls defining the exit chamber intersect the arcuate surface such that there exists, in the plane of the axes of the exit chamber and the orifice, a portion of the arcuate surface between the bottom point of the arcuate surface and the walls of the exit chamber;
    the deagglomeration chamber has a greatest cross-sectional area, in the plane normal to the axis of the orifice, greater than the cross-sectional area of the conduit chamber in the plane normal to the axis of the orifice; and
    the cross-sectional area of the exit chamber in the plane normal to its axis is less than the greatest cross-sectional area of the deagglomeration chamber in the plane normal to the axis of the orifice.

2. An actuator according to claim 1, wherein the conduit chamber is substantially in the form of a right circular cylinder.

3. An actuator according to claim 2, wherein the cylinder has a diameter of about 19 mm to about 24 mm.

4. An actuator according to claim 2, wherein the conduit chamber has a length of between about 6 mm and about 25 mm from the orifice to the region where the deagglomeration chamber begins.

5. An actuator according to claim 2, wherein the deagglomeration chamber is substantially spherical.

6. An actuator according to claim 5, wherein the deagglomeration chamber has a greatest cross-sectional area in the plane normal to the axis of the orifice of about 530 mm$^2$ to about 1130 mm$^2$.

7. An actuator according to claim 5, wherein the deagglomeration chamber has a radius of curvature greater than the radius of the conduit chamber.

8. An actuator according to claim 5, wherein the deagglomeration chamber is substantially symmetrically disposed about the axis of the orifice.

9. An actuator according to claim 1, wherein the exit chamber is substantially cylindrical.

10. An actuator according to claim 1, wherein there is a rise between the bottom point of the arcuate surface and the lowermost wall of the exit chamber.

11. An actuator according to claim 1, wherein the rise is about 3 mm to about 5 mm.

12. An actuator according to claim 1, wherein the axis of the exit chamber is disposed at an angle of about 90° to about 105° to the axis of orifice.

13. An actuator according to claim 1, wherein the cross-sectional area of the exit chamber is about 120 mm$^2$ to about 500 mm$^2$.

14. An actuator according to claim 1, comprising a top section and bottom section pressed together in a friction fit, wherein the top section has walls defining an arcuate portion substantially corresponding to the top portion of the opening between the deagglomeration chamber and the exit chamber, and wherein the top section can be rotated relative to bottom section in order to align the arcuate portion of the top section with the exit chamber.

15. An aerosol actuator adapted to receive an aerosol canister having a hollow valve stem, comprising:
    a nozzle block having walls defining at least one bleed hole and walls defining a valve stem receptacle having a socket for receiving the hollow valve stem of the aerosol canister, the socket having walls defining an orifice having a longitudinal axis through the nozzle block;
    walls defining a deagglomeration chamber in open communication with the orifice and the bleed hole, wherein the conduit chamber is substantially coaxial with the orifice and dimensioned such that it does not substantially reduce the velocity of an aerosol stream introduced via the orifice;
    walls defining a deagglomeration chamber in the form of an arcuate surface in open communication with the conduit chamber and having a bottom point; and
    walls defining an exit chamber in open communication with the deagglomeration chamber and having a longitudinal axis,
    wherein:

the walls defining the exit chamber intersect the acruate surface such that there exists, in the plane of the axes of the exit chamber and the orifice, a portion of the arcuate surface between the bottom point of the arcuate surface and the walls of the exit chamber;

the deagglomeration chamber has a greatest cross-sectional area, in the plane normal to the axis of the orifice, greater than the cross-sectional area of the conduit chamber in the plane normal to the axis of the orifice; and the cross-sectional area of the exit chamber in the plane normal to tis axis is less than the greatest cross-sectional area of the deagglomeration chamber in the plane normal to the axis of the orifice and wherein respirable particles, resulting from discharge of an aerosol canister containing an aerosol formulation through he orifice, remain suspended in the deagglomeration chamber for a time sufficient to allow a patient to inhale the formulation after discharge of the canister.

16. An aerosol actuator adapted to receive an aerosol canister having a hollow valve stem, comprising:

a nozzle block having walls defining at least one bleed hole and walls defining a valve stem receptacle having a socket for receiving the hollow valve stem of the aerosol canister, the socket having walls defining an orifice having a longitudinal axis through the nozzle block;

walls defining a deagglomeration chamber in open communication with the orifice and the bleed hole, wherein the conduct chamber is substantially coaxial with the orifice and dimensioned such that it does not substantially reduce the velocity of an aerosol stream introduced via the orifice;

walls defining a deagglomeration chamber in the form of an arcuate surface in open communication with the conduit chamber and having a bottom point; and walls defining an exit chamber in open communication with the deagglomeration chamber and having a longitudinal axis, wherein:

the walls defining the exit chamber intersect the arcuate surface such that there exists, in the plane of the axes of the exit chamber and the orifice, a portion of the arcuate surface between the bottom point of the arcuate surface and the walls of the exit chamber;

the deagglomeration chamber has a greatest cross-sectional area, in the plane normal to the axis of the orifice, greater than the cross-sectional area of the conduit chamber in the plane normal to the axis of the orifice; and the cross-sectional area of the exit chamber in the plane normal to its axis is less than the greatest cross-section area of the deagglomeration chamber in the plane normal to the axis of the orifice, in combination with an aerosol canister comprising a pharmaceutical formulation for administration by oral or nasal inhalation.

17. A method of administering a pharmaceutical formulation via inhalation therapy comprising the step of discharging a metered-dose aerosol canister comprising the formulation through an actuator according to claim 1.

* * * * *